US012595457B2

(12) United States Patent (10) Patent No.: US 12,595,457 B2
Yabuhara et al. (45) Date of Patent: Apr. 7, 2026

(54) CULTIVATION CONTAINER RACK AND ANALYZING DEVICE

(71) Applicant: Hitachi High-Tech Corporation, Tokyo (JP)

(72) Inventors: Tadao Yabuhara, Tokyo (JP); Yukie Tokiwa, Tokyo (JP); Yu Kusaka, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 960 days.

(21) Appl. No.: 17/276,374

(22) PCT Filed: Feb. 18, 2019

(86) PCT No.: PCT/JP2019/005891
§ 371 (c)(1),
(2) Date: Mar. 15, 2021

(87) PCT Pub. No.: WO2020/170313
PCT Pub. Date: Aug. 27, 2020

(65) Prior Publication Data
US 2022/0039334 A1 Feb. 10, 2022

(51) Int. Cl.
*A01G 9/24* (2006.01)
*A01G 18/60* (2018.01)
(Continued)

(52) U.S. Cl.
CPC ............ *C12M 41/14* (2013.01); *C12M 23/12* (2013.01); *C12M 23/48* (2013.01)

(58) Field of Classification Search
None
See application file for complete search history.

(56) References Cited

U.S. PATENT DOCUMENTS 3,770,591 A * 11/1973 Boirat .................... C12M 41/14
435/809
5,681,492 A * 10/1997 Van Praet ................. B01L 7/02
219/400
(Continued)

FOREIGN PATENT DOCUMENTS

EP 1 950 282 A1 7/2008
JP 1-137964 A 5/1989
(Continued)

OTHER PUBLICATIONS

Japanese-language Office Action issued in Japanese Application No. 2021-501165 dated Apr. 20, 2022 (nine (9) pages).
(Continued)

*Primary Examiner* — Brian R Gordon
(74) *Attorney, Agent, or Firm* — Crowell & Moring LLP

(57) ABSTRACT

A cultivation container rack according to the present disclosure is characterized by being provided with a cultivation container storage section for storing a cultivation container, the cultivation container storage section being provided with a first member that constitutes the top surface of the cultivation container storage section, a second member that constitutes the bottom surface of the cultivation container storage section, and a third member that is disposed on the second member and supports the cultivation container, the third member supporting the cultivation container such that the distance between the first member and the cultivation container is no greater than the distance between the second member and the cultivation container.

14 Claims, 11 Drawing Sheets

(51) Int. Cl.
 *A01G 27/00*  (2006.01)
 *C12M 1/00*  (2006.01)
 *C12M 1/32*  (2006.01)
 *C12M 3/00*  (2006.01)

(56) References Cited

U.S. PATENT DOCUMENTS

| | | | | |
|---|---|---|---|---|
| 6,004,512 | A * | 12/1999 | Titcomb | G01N 1/312 |
| | | | | 422/417 |
| 6,251,659 | B1 * | 6/2001 | Fukuzuno | C12M 41/12 |
| | | | | 422/65 |
| 12,000,848 | B2 * | 6/2024 | Verhoef | C12M 1/268 |
| 2001/0050276 | A1 * | 12/2001 | Inami | F27B 17/02 |
| | | | | 219/400 |
| 2004/0112980 | A1 * | 6/2004 | Reichel | B01L 3/0268 |
| | | | | 239/102.1 |
| 2006/0141609 | A1 | 6/2006 | Kagayama et al. | |
| 2011/0143425 | A1 * | 6/2011 | Toguchida | C12M 23/52 |
| | | | | 435/286.1 |
| 2012/0083030 | A1 * | 4/2012 | Busujima | C12M 37/00 |
| | | | | 435/303.1 |
| 2016/0017271 | A1 | 1/2016 | Nozaki et al. | |
| 2018/0257079 | A1 * | 9/2018 | Wong | G01N 35/00584 |
| 2018/0371394 | A1 * | 12/2018 | Ho | C12M 29/24 |
| 2019/0024036 | A1 * | 1/2019 | Hitomi | C12M 41/48 |
| 2020/0010792 | A1 * | 1/2020 | Golway | C12M 29/10 |
| 2020/0018774 | A1 | 1/2020 | Masuya et al. | |
| 2020/0088750 | A1 * | 3/2020 | Reinhardt | B01L 9/52 |
| 2021/0147785 | A1 * | 5/2021 | Buzalewicz | C12M 41/12 |

FOREIGN PATENT DOCUMENTS

| | | | |
|---|---|---|---|
| JP | 2003-93044 A | | 4/2003 |
| JP | 2006-39171 A | | 2/2006 |
| JP | 2006039171 | * | 2/2006 |
| JP | 2006-61126 A | | 3/2006 |
| JP | 2007-166982 A | | 7/2007 |
| JP | 2010-158185 A | | 7/2010 |
| JP | 2011-200223 A | | 10/2011 |
| JP | 2015-89363 A | | 5/2015 |
| WO | WO 2014/155500 A1 | | 10/2014 |
| WO | WO 2018-179081 A1 | | 10/2018 |

OTHER PUBLICATIONS

International Search Report (PCT/ISA/210) issued in PCT Application No. PCT/JP2019/005891 dated Apr. 23, 2019 with English translation (four (4) pages).

Japanese-language Written Opinion (PCT/ISA/237) issued in PCT/JP2019/005891 dated Apr. 23, 2019 (five (5) pages).

Extended European Search Report issued in European Application No. 19916259.5 dated Sep. 5, 2022 (eight (8) pages).

* cited by examiner

[FIG. 1A]
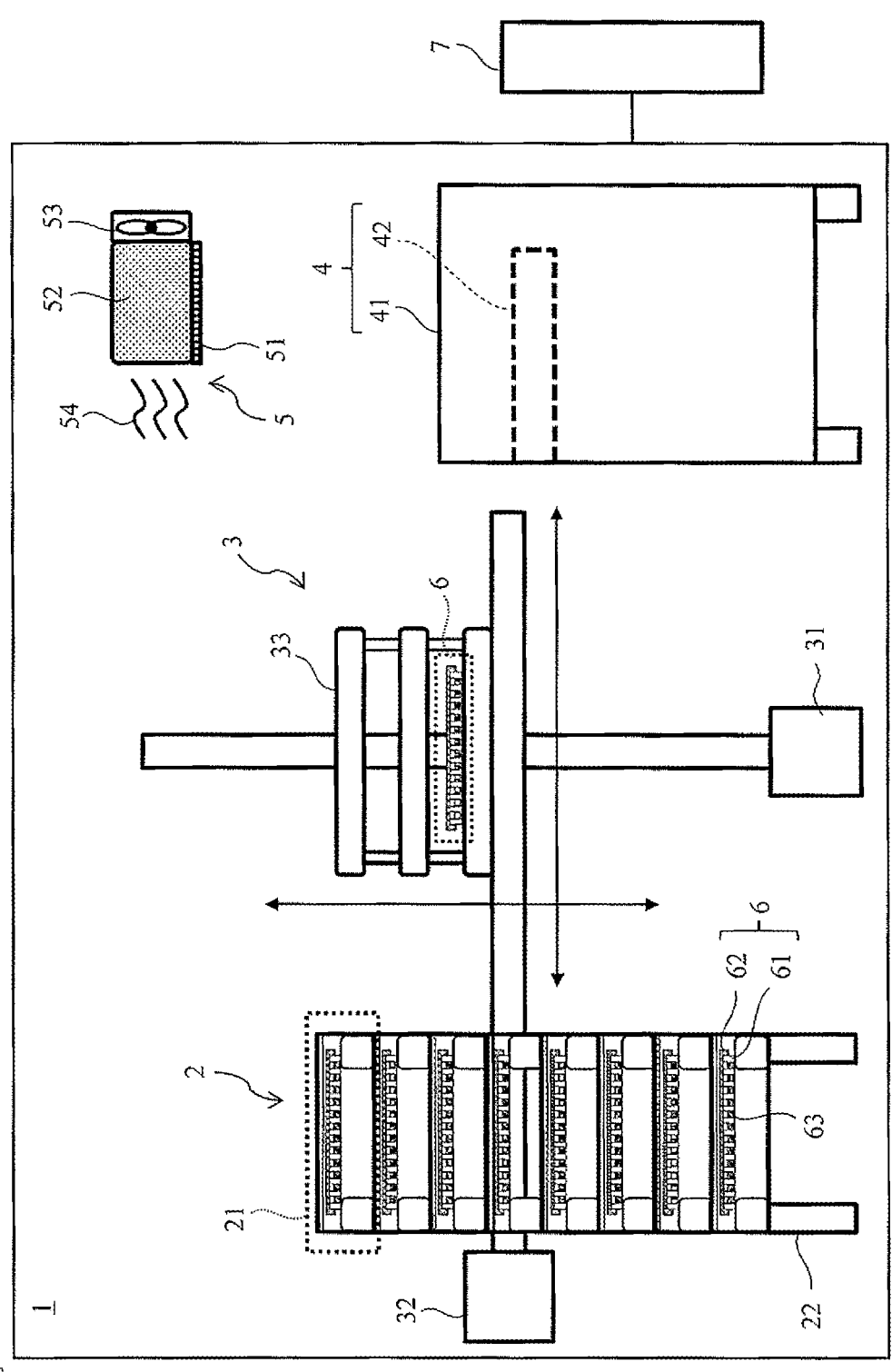

[FIG. 1B]
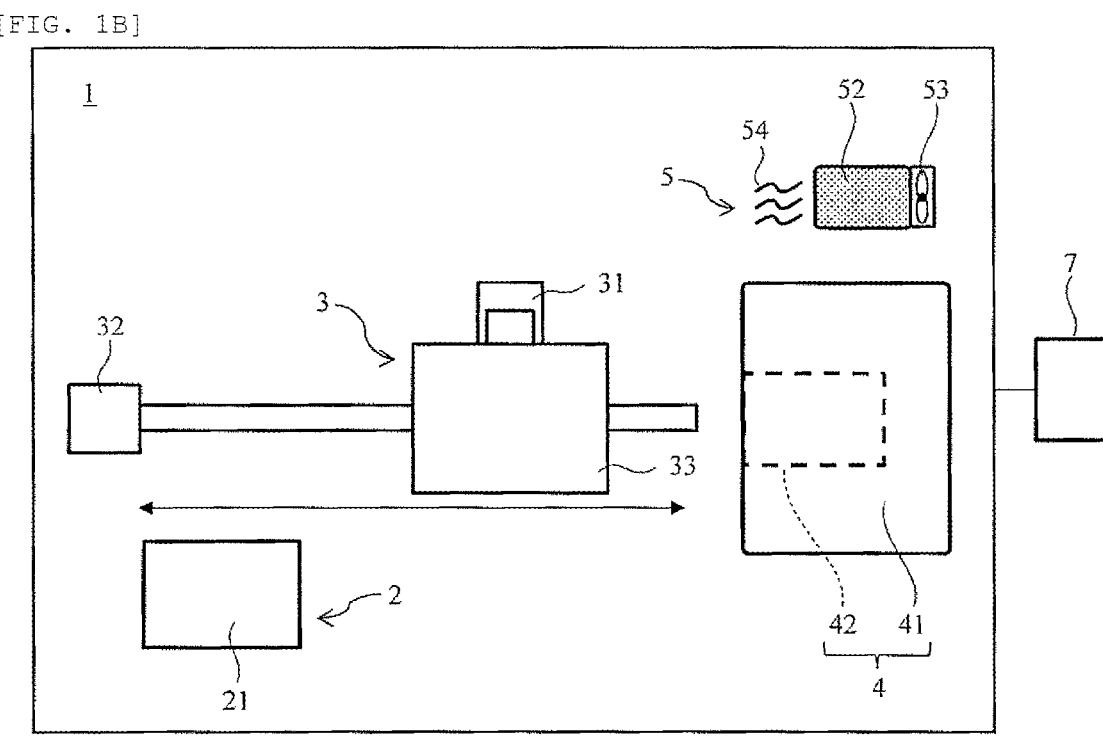
[FIG. 1C]
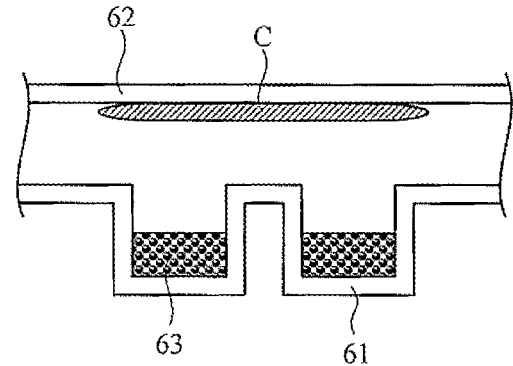

[FIG. 1D]
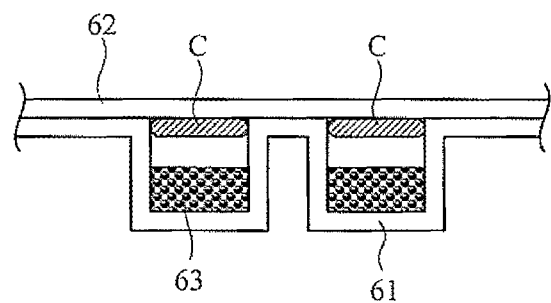
[FIG. 2A]
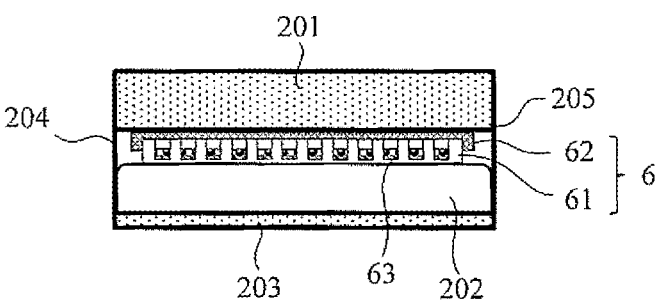
[FIG. 2B]
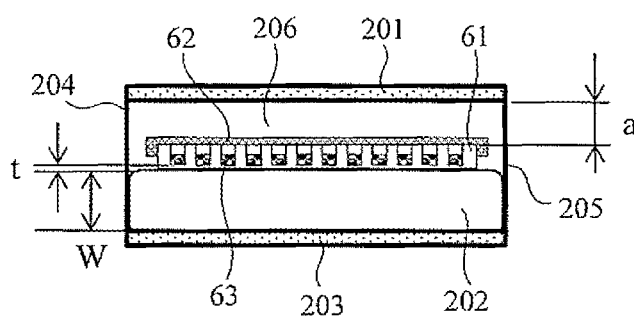

[FIG. 2C]
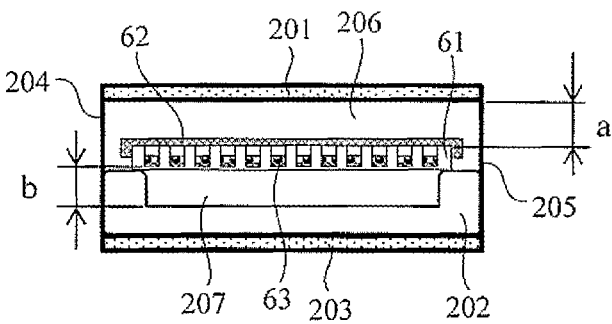
[FIG. 2D]
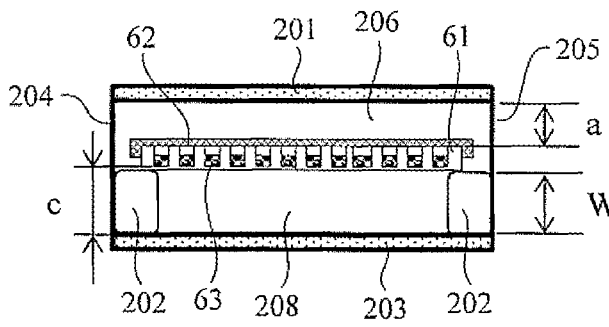
[FIG. 2E]
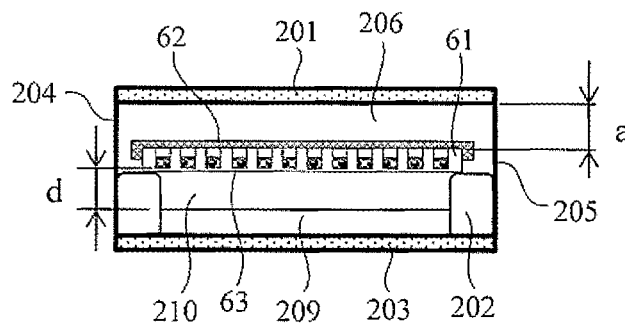

[FIG. 2F]
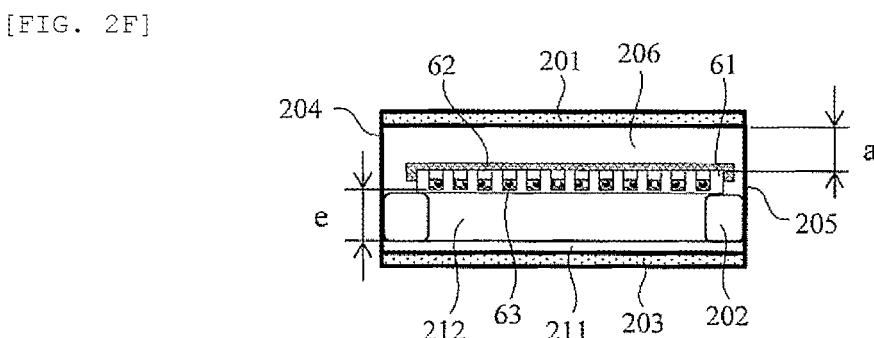
[FIG. 3A]
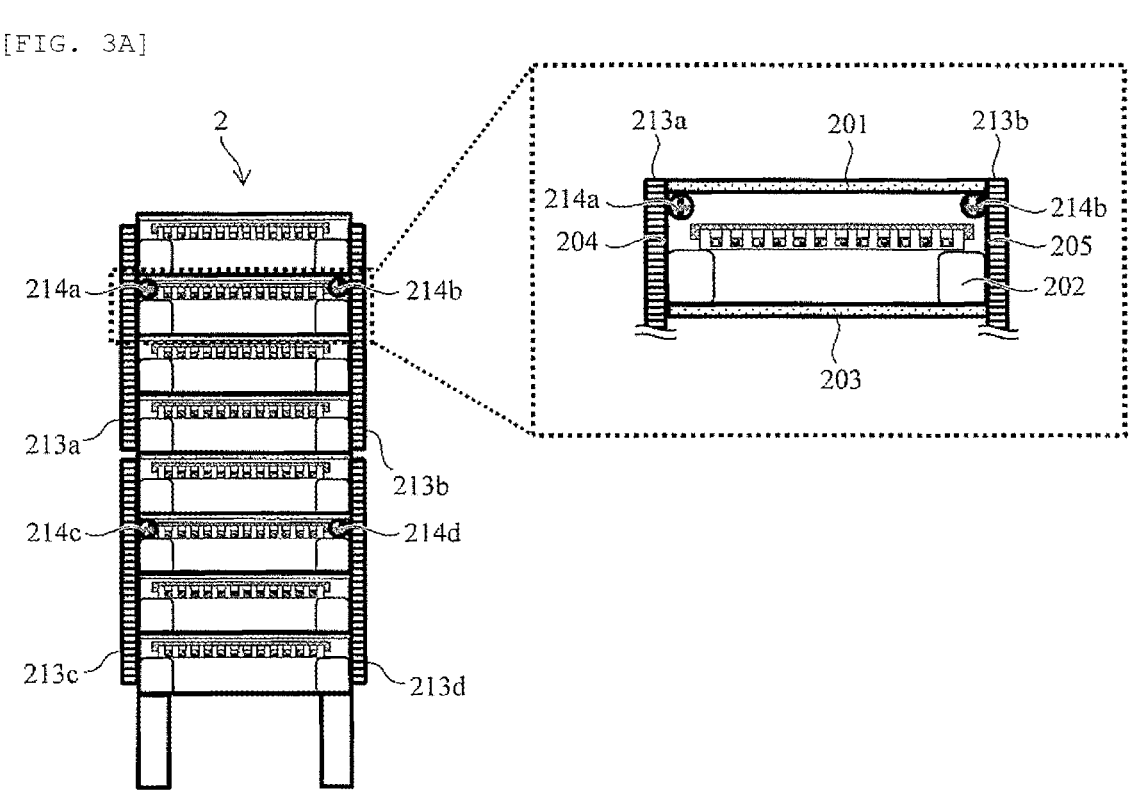

[FIG. 3B]
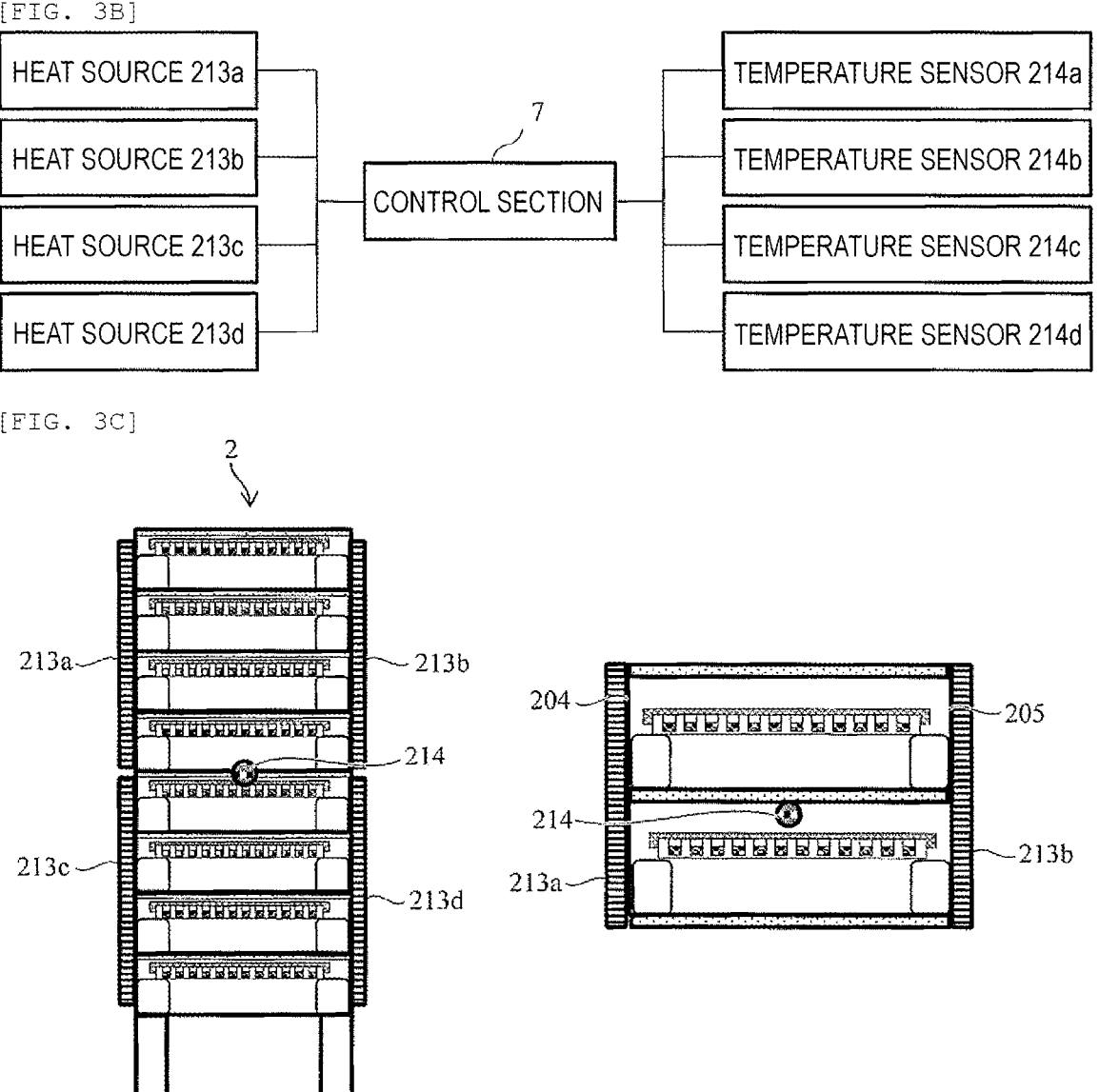
[FIG. 3C]

[FIG. 3D]
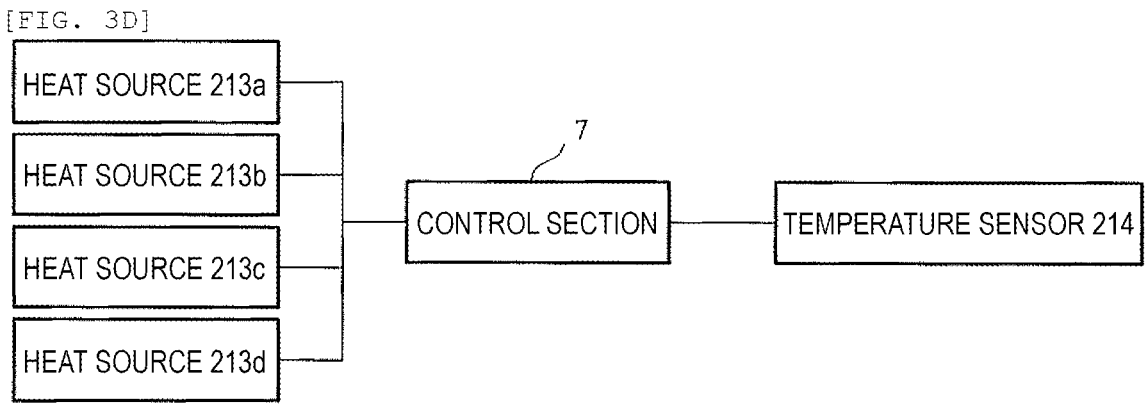

[FIG. 3E]
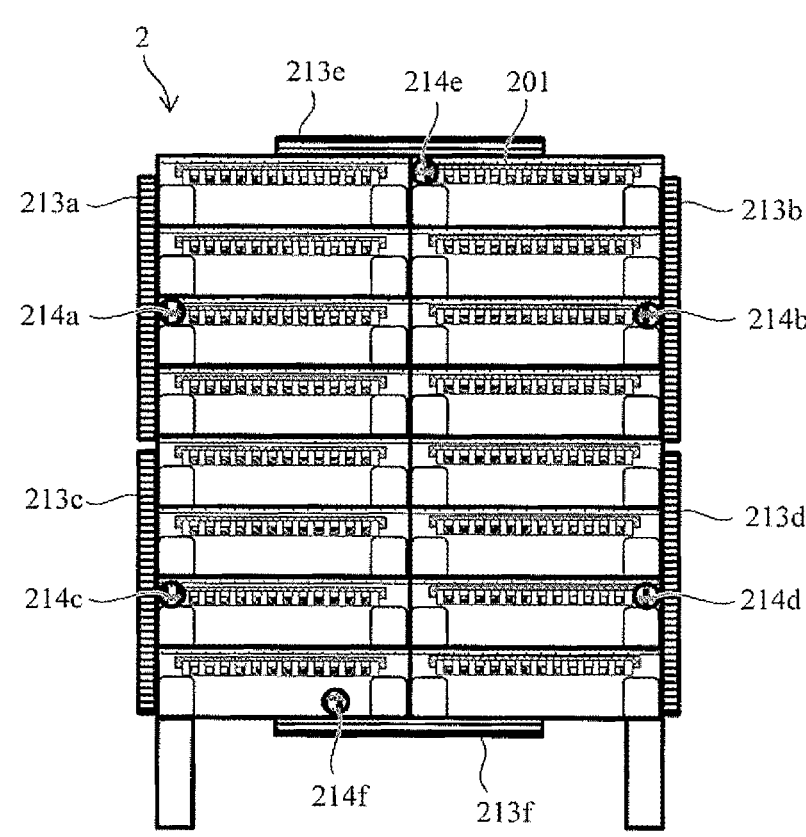

[FIG. 3F]
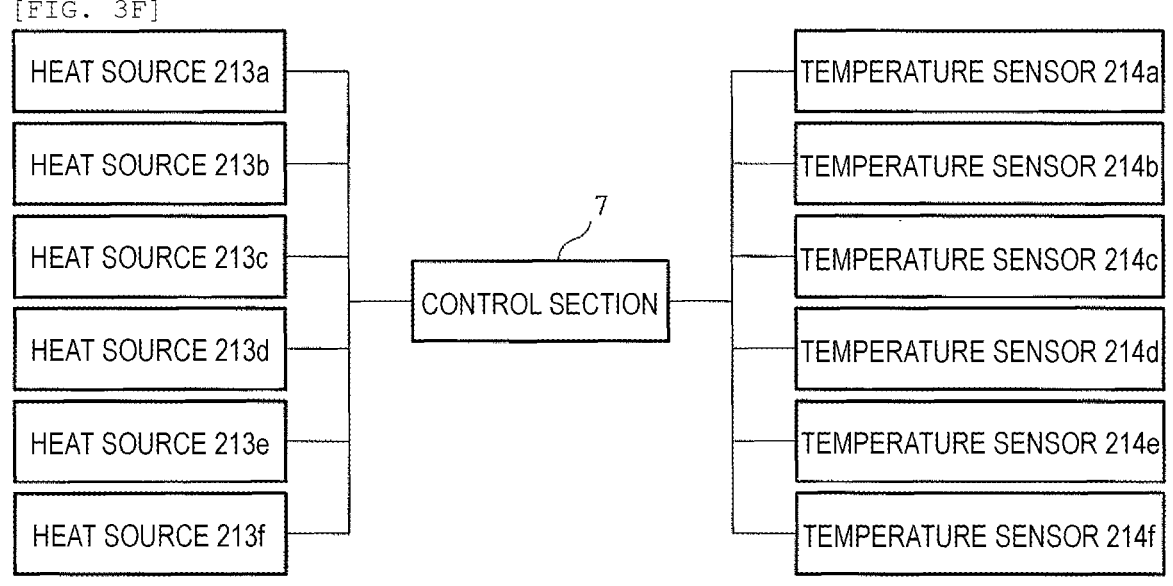

[FIG. 3G]
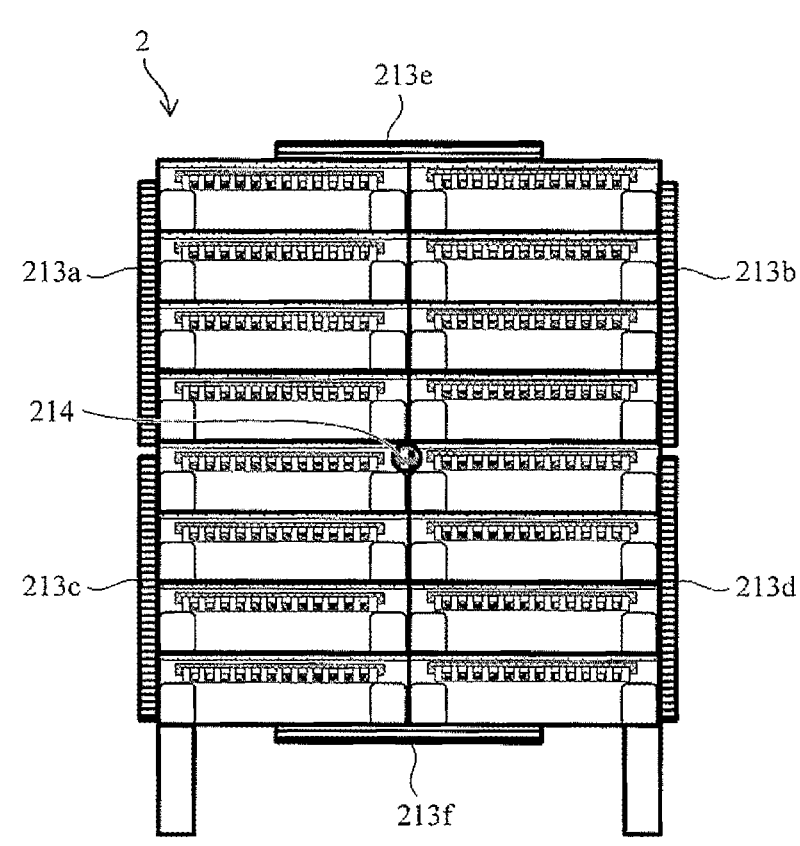

[FIG. 3H]
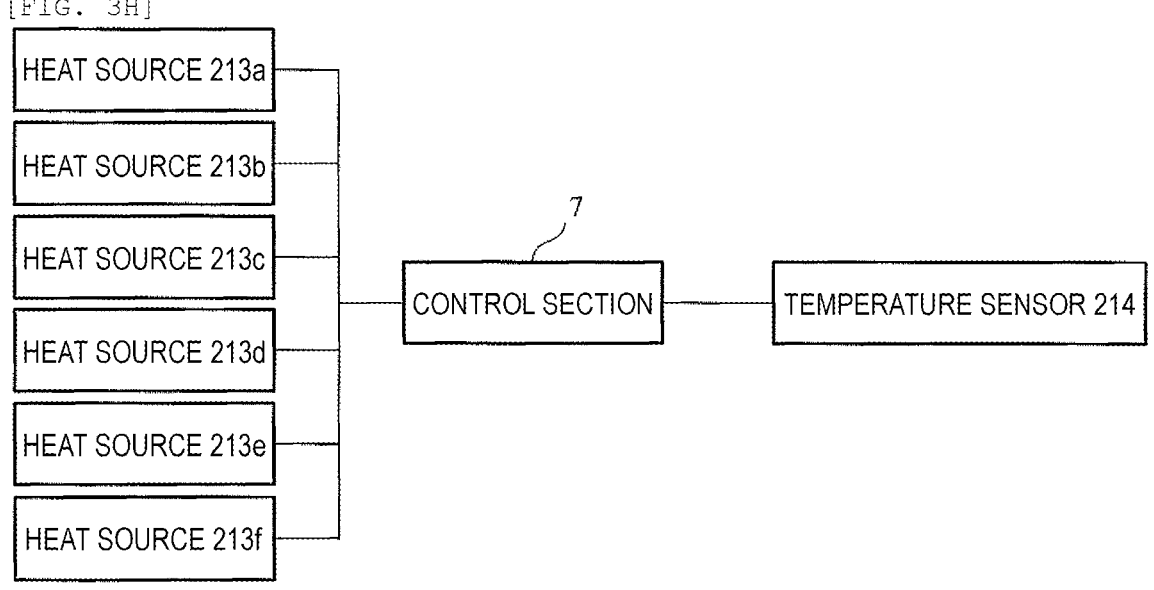

CULTIVATION CONTAINER RACK AND ANALYZING DEVICE

TECHNICAL FIELD

The present disclosure relates to a cultivation container rack and an analyzing device.

BACKGROUND ART

At medical research institutes, hospitals, and the like, tests are carried out by cultivating cells and bacteria in samples for microscope observation or turbidity measurement. In cell cultivation and bacterial cultivation, a microwell plate or a petri dish is used as a sample container, and pretreated samples and nutrients are introduced into the sample container and cultivated. The sample inoculated in the sample container is repeatedly cultivated in the incubator and observed with a measuring device for a long period of time, and changes in the cultivation state are analyzed.

However, if the cultivation and observation are repeated for a long period of time, dew condensation occurs on the lid of the sample container or the like due to the temperature gradient in the incubator. Water droplets caused by dew condensation, for example, cause refraction of light in transmission observation and are led to deterioration of contrast and erroneous determination of a turbidity value caused by a decrease in the amount of light.

As a cultivation observation device that suppresses the occurrence of the dew condensation in the sample container, for example, JP-A-2010-158185 (PTL 1) discloses "when a cultivation container 14 is introduced into an incubator section 12, the cultivation container 14 is placed on a base section 35, and a heater 36 heats a cultivation container until an arm 31 of a conveyance robot 15 introduces the cultivation container 14 placed on the base section 35" (see Abstract of PTL 1).

JP-A-2007-166982 (PTL 2) discloses a biological sample cultivation observation device, in which "as illustrated in FIGS. 1 and 3, a hot air supply nozzle (gas blowing means) 25 that blows hot air (gas) H of which the temperature is adjusted to a predetermined temperature is provided to a housing 7 of an incubator box 2 so that the inside of a cultivation environment E becomes a temperature appropriate for cultivation with respect to an inner surface 5a of a transparent plate 5" (see Paragraph of PTL 2).

CITATION LIST

Patent Literature

PTL 1: JP-A-2010-158185
PTL 2: JP-A-2007-166982

SUMMARY OF INVENTION

Technical Problem

However, in PTL 1, the number of cultivation containers that can be introduced into the device is one. Therefore, when measurement is performed by using a plurality of cultivation containers, waiting time is required for the user in case of additional introduction of the cultivation container, and thus the user cannot leave the device. It is possible to reduce the waiting time by providing the plurality of base sections, but the plurality of base sections are required, so that the cost of the mechanical parts increases, and the size of the device also increases.

In PTL 2, in order to prevent the occurrence of the dew condensation on the transparent plate, hot air is blown to the inner surface of the transparent plate inside the incubator box, and the transparent plate is heated, so that the water droplets generated by the evaporation of humidified water are hardly formed on the transparent plate. However, only one cultivation container can be installed. Accordingly, when a plurality of cultivation containers are observed, the plurality of same devices are required, and thus the cost increases, to increase the device size and to increase the number of consumables such as cultivation gas and humidified water.

Herein, the present disclosure provides a cultivation container rack and an analyzing device that prevent the occurrence of the dew condensation in the cultivation container.

Solution to Problem

According to the present disclosure, a cultivation container rack includes a cultivation container storage section that stores a cultivation container, in which the cultivation container storage section includes a first member that configures a top surface of the cultivation container storage section, a second member that configures a bottom surface of the cultivation container storage section, and a third member that is disposed on the second member and supports the cultivation container, and the third member supports the cultivation container so that a distance between the first member and the cultivation container is no greater than a distance between the second member and the cultivation container.

Other characteristics relating to the disclosure become apparent from the description of the present specification and the accompanying drawings. The aspects of the present disclosure are achieved and realized by elements, the combination of various elements, and the aspects of the following detailed description and the accompanying claims.

It should be understood that the description of the present specification is merely an exemplary example and is not intended to limit the claims or applications of the present disclosure in any way.

Advantageous Effects of Invention

According to the present disclosure, the occurrence of the dew condensation in the cultivation container can be prevented.

Objects, configurations, and effects in addition to the above are clarified by the following description of the embodiments.

BRIEF DESCRIPTION OF DRAWINGS

FIG. 1A is a schematic front view illustrating the entire configuration of an analyzing device according to a first embodiment.

FIG. 1B is a schematic plan view illustrating the entire configuration of the analyzing device according to the first embodiment.

FIG. 1C is a schematic diagram illustrating a place where dew condensation occurs.

FIG. 1D is a schematic diagram illustrating the place where dew condensation occurs.

FIG. 2A is a schematic front view illustrating a configuration example of a cultivation container storage section.

FIG. 2B is a schematic front view illustrating a configuration example of the cultivation container storage section.

FIG. 2C is a schematic front view of a configuration example of the cultivation container storage section.

FIG. 2D is a schematic front view illustrating a configuration example of the cultivation container storage section.

FIG. 2E is a schematic front view illustrating a configuration example of the cultivation container storage section.

FIG. 2F is a schematic front view illustrating a configuration example of the cultivation container storage section.

FIG. 3A is a schematic front view of a disposition example of a heat source and a temperature sensor according to a second embodiment.

FIG. 3B is a block diagram illustrating a control mechanism of the heat source and the temperature sensor of FIG. 3A.

FIG. 3C is a schematic front view illustrating a disposition example of the heat source and the temperature sensor according to the second embodiment.

FIG. 3D is a block diagram illustrating a control mechanism of the heat source and the temperature sensor of FIG. 3C.

FIG. 3E is a schematic front view illustrating a disposition example of the heat source and the temperature sensor according to the second embodiment.

FIG. 3F is a block diagram illustrating a control mechanism of the heat source and the temperature sensor of FIG. 3E.

FIG. 3G is a schematic front view illustrating a disposition example of the heat source and the temperature sensor according to the second embodiment.

FIG. 3H is a block diagram illustrating a control mechanism of the heat source and the temperature sensor of FIG. 3G.

DESCRIPTION OF EMBODIMENTS

First Embodiment

FIG. 1A is a schematic front view illustrating the entire configuration of an analyzing device 1 according to a first embodiment, and FIG. 1B is a schematic plan view thereof. As illustrated in FIGS. 1A and 1B, the analyzing device 1 includes a cultivation container rack 2, a conveyance section 3, a measuring section 4, a temperature control section 5, and a control section 7.

The cultivation container rack 2 includes eight stages of cultivation container storage sections 21 stacked in the height direction, and one cultivation container 6 is stored in each of the cultivation container storage sections 21. Leg sections 22 that support the cultivation container storage sections 21 are installed in the lower part of the cultivation container storage section 21 on the lowermost stage. The number of the cultivation container storage sections 21 is not limited to eight, and the number of stages may be increased or may be decreased. The analyzing device 1 may include the plurality of cultivation container racks 2. Details of the cultivation container storage section 21 are described below.

The cultivation container 6 is configured with a sample container 61 and a lid 62. The sample container 61 is, for example, a well plate including a plurality of wells such as a 96-well plate and a 384-well plate, and samples 63 are inoculated into each well. Examples of the sample 63 include cells, blood, urine, bacteria, and tissues. The lid 62 may have a seal shape.

The conveyance section 3 includes actuators 31 and 32 and a holding section 33, and is configured so that the cultivation containers 6 can be conveyed. The holding section 33 is configured so that the cultivation containers 6 are held and moved in the height direction and the horizontal direction by the actuators 31 and 32. The actuators 31 and 32 are configured with, for example, a ball screw or a belt. The holding section 33 can receive and deliver the cultivation containers 6 with a mechanism (not illustrated).

Though not illustrated, the holding section 33 may include a first holding section that holds the cultivation container 6 to be measured next in the measuring section 4 and a second holding section that holds the cultivation container 6 measured in the measuring section 4. The measured cultivation container 6 may be extracted from the measuring section 4, and the unmeasured cultivation container 6 may be introduced to the measuring section 4.

The measuring section 4 includes a measuring unit 41 and a sample measuring section 42. The sample measuring section 42 is in the measuring unit 41, and is a measuring device that measures a cultivation state of the samples 63 in each well of the cultivation container 6. The sample measuring section 42 includes various mechanisms (not illustrated) for performing, for example, turbidity measurement, absorbance measurement, fluorescence measurement, and image analysis.

The temperature control section 5 includes a heater 51, a heat sink 52, and a fan 53, and adjusts the temperature in the analyzing device 1. The heat of the heater 51 is supplied to the analyzing device 1 through wind 54 generated by the fan 53 via the heat sink 52. As the heater 51, for example, a heater such as an electric heater, a ceramic heater, a silicon rubber heater, a sheathed heater, a band heater, a polyimide heater, a space heater, a cord heater, a cartridge heater, or a metal embedded heater can be used. In addition to such heaters, Peltier may be used. As the material of the heat sink 52, for example, aluminum, copper, iron, and stainless steel can be used.

The control section 7 is, for example, a computer such as a personal computer, and controls an operation of the entire analyzing device 1. The control section 7 is connected to the conveyance section 3, the measuring section 4, and the temperature control section 5 by wire or wirelessly, and transmits an instruction to each of the mechanisms or receives an output of each mechanism.

Though not illustrated, the control section 7 may include a display section that displays a measurement result and the like in the sample measuring section 42, a data processing section that calculates an amount of change of the cultivation state of the samples 63 over time based on the measurement result, an input section that enables the user to input an instruction, and a storage section that stores a measurement result. The control section 7 may be embedded in the measuring unit 41.

The measuring unit 41 may include a temperature sensor (not illustrated) that measures the temperature of the sample measuring section 42. Here, the control section 7 controls an output of the heat quantity of the heater 51 based on the output value of the temperature sensor.

Subsequently, an operation of the analyzing device 1 is described. First, the user stores the cultivation container 6 to which the samples 63 are inoculated in each the cultivation container storage section 21. Thereafter, the user inputs an instruction for starting an operation of the analyzing device 1 with an input section of the control section 7 or the like.

If the instruction for starting an operation is received, the control section 7 drives the conveyance section 3. The conveyance section 3 receives the cultivation container 6 from the cultivation container storage section 21 and conveys the cultivation container 6 to the sample measuring section 42. If the conveyance of the cultivation container 6 is completed, the control section 7 drives the sample measuring section 42, and the sample measuring section 42 measures the cultivation states of the samples 63 in the sample container 61 (Step S1). Here, the control section 7 may receive the measurement result from the sample measuring section 42 and cause the measurement result to be displayed on a display section (not illustrated).

If the measurement ends by the sample measuring section 42, the control section 7 drives the conveyance section 3. The conveyance section 3 moves and stores the cultivation container 6 from the sample measuring section 42 into the cultivation container storage section 21. The samples 63 in the cultivation container 6 are cultivated for a predetermined period of time in the cultivation container storage section 21 (Step S2).

For one cultivation container 6, the control section 7 repeats the measurement cycle of Steps S1 and S2, for example, at an interval of 20 to 30 minutes for about 18 hours. While in a certain cultivation container storage section 21, the samples 63 in the cultivation container 6 are cultivated, the samples 63 of the cultivation container 6 stored in another cultivation container storage section 21 are measured.

In the cultivation and measurement of the sample in the analyzing device 1 as described above, generally, the time for which the cultivation container 6 is stored in the cultivation container storage section 21 (cultivation time) is longer than the measurement time in the sample measuring section 42. Generally, when the cultivation container 6 in the incubator is installed, the thermal energy supplied from the material of the member that supports the lower surface of the sample container 61 or the air present in the little unevenness on the lower surface of the sample container 61 to the samples 63 in the sample container 61 becomes higher than the thermal energy supplied to the lid 62. Accordingly, the dew condensation occurs inside the cultivation container 6.

FIG. 1C is a schematic diagram illustrating the place where dew condensation occurs when there is a gap between the sample container 61 and the lid 62. FIG. 1C illustrates only a portion of the cultivation container 6 for simplification of the illustration. As illustrated in FIG. 1C, when there is a gap between the sample container 61 and the lid 62 of the cultivation container 6, the dew condensation C occurs between the upper surface of the sample container 61 and the bottom surface of the lid 62.

FIG. 1D is a schematic diagram illustrating the place where dew condensation occurs when there is no gap between the sample container 61 and the lid 62. FIG. 1D illustrates only a portion of the cultivation container 6 for simplification of the illustration. As illustrated in FIG. 1D, if there is no gap between the sample container 61 and the lid 62, the dew condensation C occurs on the interface between an open end of each well of the sample container 61 and the lid 62.

In the present specification, the places where the dew condensation C occurs as described above (the interface between the upper surface of the sample container 61 and the bottom surface of the lid 62, and the interface of an open end of each well of the sample container 61 and the lid 62) may be referred to as dew condensation occurrence sections.

Therefore, suggested is the cultivation container storage section 21 that can prevent or remove the dew condensation occurring in the dew condensation occurrence section during the waiting time until the next measurement. Hereinafter, the cultivation container storage section 21 that uses a container without a gap between the sample container 61 and the lid 62 as the cultivation container 6, and that prevents the dew condensation occurring on the interface between the open end of the sample container 61 and the lid 62 is described.

FIG. 2A is a schematic front view illustrating a configuration example of the cultivation container storage section 21 according to the present embodiment. As illustrated in FIG. 2A, the cultivation container storage section 21 includes a metal material 201 (first member), a heat insulating material 202 (third member), a metal material 203 (second member), a metal material 204, and a metal material 205.

The metal material 201 configures the top surface of the cultivation container storage section 21, and the metal material 203 configures the bottom surface of the cultivation container storage section 21. The lower surface of the metal material 201 faces the upper surface of the lid 62. The heat insulating material 202 is disposed on the metal material 203, and is in contact with the lower surface of the sample container 61 when the cultivation container 6 is stored to support the sample container 61. In other words, the cultivation container 6 is stored between the metal material 201 and the heat insulating material 202. The metal materials 204 and 205 respectively configure side surfaces of the cultivation container storage sections 21. As such, the cultivation container 6 is surrounded with the metal materials 201, 203, 204, and 205 on the top, bottom, left and right and can be stored or extracted from the front side and the rear side of the cultivation container storage section 21.

If the plurality of stages of the cultivation container storage sections 21 are provided, the metal material 203 of the cultivation container storage section 21 positioned on the upper stage and the metal material 201 of the cultivation container storage section 21 positioned on the lower stage may be in contact with each other or another member may be disposed therebetween. The metal material 201 of the cultivation container storage section 21 positioned on the lower stage may also be used as the metal material 203. With respect to the cultivation container storage section 21 positioned on the lowermost stage of the cultivation container rack 2, only the metal material 203 is disposed on the lower surface of the heat insulating material 202.

As the material of the metal materials 201, 203, 204, and 205, for example, aluminum, stainless steel, copper, iron, and titanium can be used. As the heat insulating material 202, for example, glass wool, a cellulose fiber, an insulation board, a wool heat insulating material, rock wool, hard urethane foam, beaded polystyrene foam, phenol foam, vacuum heat insulating material, and resin material can be used. Examples of the resin material include polyamide, POM, PEEK, PPS, PTFE, PVC, PE, PP, PS, and ABS.

As described above, the cultivation container storage section 21 has a structure in which the cultivation container 6 is surrounded on the top, bottom, left, and right, and thus heat convection hardly occurs around the cultivation container 6.

Generally, owing to the room temperature of the room where the analyzing device 1 is installed and the thermal energy supplied from the temperature control section 5, the cultivation container storage section 21 is balanced with a certain temperature distribution. Here, in order to prevent the dew condensation, in such a balanced state, the thermal conductivity of the member (the metal material 201) in contact with the upper surface of the lid 62 is caused to be higher than the thermal conductivity of the member (the heat insulating material 202) in contact with the lower surface of the sample container 61, so that the supply amount of the thermal energy to the interface between the open end of the sample container 61 and the lid 62 is more than the supply amount of the thermal energy to the samples 63 in the sample container 61. The thermal conductivity of the heat insulating material 202 is caused to be lower than the thermal conductivity of the metal material 203. In addition, the thermal conductivity of the metal material 201 may be caused to be higher than the thermal conductivity of the metal material 203.

By employing the cultivation container storage section 21 with such configuration, the thermal energy supplied to the interface between the open end of the sample container 61 and the lid 62 becomes greater than the thermal energy supplied to the interfaces between the inner bottom sections of the sample container 61 (wells) and the samples 63, and the temperature of the upper surface of the lid 62 becomes higher than the temperature of the lower surface of the sample container 61. Therefore, the occurrence of the dew condensation on the interface between the open end of the sample container 61 and the lid 62 can be prevented.

FIG. 2B is a schematic front view illustrating another configuration example of the cultivation container storage section 21. The cultivation container storage section 21 of FIG. 2B is different from that of FIG. 2A in that an air layer 206 (first air layer) is provided between the upper surface of the lid 62 and the lower surface of the metal material 201. The other configurations are the same as those in FIG. 2A and thus the descriptions thereof are omitted.

A thickness a of the air layer 206 (a distance between the first member and the cultivation container) is defined as a distance from the lower surface of the metal material 201 to the interface between the open end of the sample container 61 and the lid 62. The thickness a of the air layer 206 is appropriately set according to the material of the metal material 201 or the heat insulating material 202, in the range in which a relational expression of the thermal energy supplied to the interfaces between the inner bottom sections of the sample container 61 and the samples 63 (heat conduction+heat transfer+radiation) is smaller than the thermal energy supplied to the interface of the open end of the sample container 61 and the lid 62 (heat conduction+heat transfer+radiation).

A distance from the upper surface of the heat insulating material 202 to the interfaces between the inner bottom sections of the sample container 61 and the samples 63 is t. The thickness of the heat insulating material 202 is W. As illustrated in FIG. 2B, W+t is the same as the distance from the upper surface of the metal material 203 to the interfaces between the inner bottom sections of the sample container 61 and the samples 63 (a distance between the second member and the cultivation container). Here, if the thermal conductivity of the heat insulating material 202 is no greater than the thermal conductivity of the air, a is smaller than W+t. Accordingly, the thermal energy applied by the metal material 201 to the interface between the open end of the sample container 61 and the lid 62 can be caused to be higher than the thermal energy to the interfaces between the inner bottom sections of the sample container 61 and the samples 63, and thus the dew condensation can be prevented.

In the configuration of FIG. 2B, the surface shape of the lower surface of the metal material 201 that faces the lid 62 may be caused to be uneven, the lower surface of the metal material 201 may be subjected to a surface treatment (for example, an alumite treatment) so that a color having a high emissivity may be applied to the emissivity increases, or the lower surface of the metal material 201. By employing such a configuration, the thermal energy of the radiation applied by the metal material 201 to the interface between the open end of the sample container 61 and the lid 62 can be further increased, so that the dew condensation can be prevented.

FIG. 2C is a schematic front view illustrating another configuration example of the cultivation container storage section 21. The cultivation container storage section 21 of FIG. 2C is different from that of FIG. 2B in that the heat insulating material 202 is formed in a substantially U shape, and an air layer 207 (second air layer) is formed under the place where the samples 63 of the sample container 61 are housed. As illustrated in FIG. 2C, the heat insulating material 202 supports the left and right ends of the sample container 61. A thickness b of the air layer 207 is defined as a distance from the interface between the inner bottom sections of the sample container 61 and the samples 63 to the upper surface of the concave section of the heat insulating material 202.

For example, if a material with the thermal conductivity higher than that of the air (for example, about 10 times) is used as the heat insulating material 202, the thermal energy supplied to the interface between the inner bottom sections of the sample container 61 and the samples 63 can be caused to be lower than that that in FIG. 2B, by providing the air layer 207 in the heat insulating material 202 as illustrated in FIG. 2C.

As described above, by employing the structure illustrated in FIG. 2C, the thermal energy supplied to the interfaces between the inner bottom sections of the sample container 61 and the samples 63 can be caused to be lower than the thermal energy supplied to the interface between the open end of the sample container 61 and the lid 62, and accordingly the dew condensation can be prevented.

FIG. 2D is a schematic front view illustrating another configuration example of the cultivation container storage section 21. The cultivation container storage sections 21 of FIG. 2D is different from that of FIG. 2C in that the heat insulating material 202 is not present (is not charged) under the place where the samples 63 of the sample container 61 are housed, and an air layer 208 (second air layer) is provided between the lower surface of the sample container 61 and the upper surface of the metal material 203.

As illustrated in FIG. 2D, the heat insulating material 202 is used as a scaffold that supports the left and right ends of the lower surface of the sample container 61, and the thermal energy can be positively supplied to the metal materials 201 and 203. In the configuration of FIG. 2D, by causing the thermal conductivity of the metal material 201 to be higher than that of the metal material 203, the thermal energy supplied to the interface between the open end of the sample container 61 and the lid 62 can become greater than the thermal energy supplied to the interfaces between the inner bottom sections of the sample container 61 and the samples 63.

A thickness c of the air layer 208 is defined as a distance from the interfaces between the inner bottom sections of the sample container 61 and the samples 63 to the upper surface of the metal material 203. If the material and the surface state of the upper surface of the metal material 203 are the same as those of the lower surface of the metal material 201, in order to effectively supply the radiant heat from the metal material 201 to the upper surface of the cultivation container 6, a thickness W of the heat insulating material 202 is set so that the thickness a of the air layer 206 is smaller than the thickness c of the air layer 208.

The thickness a of the air layer 206 may be the same as the thickness c of the air layer 208, and here, the surface shape of the lower surface of the metal material 201 that faces the upper surface of the lid 62 is rougher than the upper surface of the metal material 203 that faces the lower surface of the sample container 61. Otherwise, the surface treatment of the lower surface of the metal material 201 is different from the surface treatment of the upper surface of the metal material 203. For example, if aluminum is used as the metal materials 201 and 203, an alumite treatment is performed on the lower surface of the metal material 201, and only a degreasing treatment is performed on the upper surface of the metal material 203. Accordingly, the radiation energy to the interface between the lid 62 and the sample container 61 can be higher than the radiation energy to the interfaces between the inner bottom sections of the sample container 61 and the samples 63, and thus the dew condensation can be prevented.

The radiation energy supplied to the interface between the lid 62 and the sample container 61 may be caused to be higher than the radiation energy supplied to the interfaces between the inner bottom sections of the sample container 61 and the samples 63 by causing the color of the lower surface of the metal material 201 to be different from the color of the upper surface of the metal material 203.

Here, the emissivity of the lower surface of the metal material 201 is different from the emissivity of the upper surface of the metal material 203, the thickness W of the heat insulating material 202 is be set so that the thickness a of the air layer 206 is smaller than the thickness c of the air layer 208×√(the emissivity of the lower surface of the metal material 201/the emissivity of the upper surface of the metal material 203). Accordingly, the occurrence of the dew condensation can be prevented. If the relational expression of the thermal energy supplied to the interfaces between the inner bottom sections of the sample container 61 and the samples 63 (heat conduction+heat transfer+radiation) is smaller than the thermal energy supplied to the interface of the open end of the sample container 61 and the lid 62 (heat conduction+heat transfer+radiation), the emissivity of the metal material 201 is higher than the emissivity of the metal material 203, and the thermal conductivity of the metal material 201 can be lower than the thermal conductivity of the metal material 203.

As above, also in the cultivation container storage section 21 illustrated in FIG. 2D, the thermal energy supplied to the interface between the open end of the sample container 61 and the lid 62 can be caused to be greater than the thermal energy supplied to the interfaces between the inner bottom sections of the sample container 61 and the samples 63, and thus the occurrence of the dew condensation in the dew condensation occurrence section can be prevented.

FIG. 2E is a schematic front view illustrating another configuration example of the cultivation container storage section 21. The cultivation container storage section 21 of FIG. 2E different from that of FIG. 2D in that a heat insulating material 209 with the thermal conductivity lower than that of the air is disposed on the upper surface of the metal material 203. The thickness of the heat insulating material 209 can be caused to be a thickness so that an air layer 210 (second air layer) is formed between the lower surface of the sample container 61 and the upper surface of the heat insulating material 209.

A thickness d of the air layer 210 is defined as a distance from the interfaces between the inner bottom sections of the sample container 61 and the samples 63 to the upper surface of the heat insulating material 209. In the cultivation container storage section 21 of FIG. 2E, a relationship of the thickness a of the air layer 206 may be set to be smaller than the thickness d of the air layer 210. Accordingly, the supply amount of the thermal energy to the lower surface of the sample container 61 can be decreased, and thus the occurrence of the dew condensation can be prevented.

The heat insulating material 209 is not necessarily required to be in contact with the upper surface of the metal material 203, and can be disposed in any position as long as the position is between the lower surface of the sample container 61 and the upper surface of the metal material 203. For example, in addition to the air layer 210 on the heat insulating material 209, the air layer may be formed between the lower surface of the heat insulating material 209 and the upper surface of the metal material 203. If the thermal conductivity of the heat insulating material 209 is no greater than the thermal conductivity of the air, the heat insulating material 209 may be disposed so that the upper surface of the heat insulating material 209 and the bottom surface of the sample container 61 are in contact with each other.

FIG. 2F is a schematic front view illustrating another configuration example of the cultivation container storage section 21. The cultivation container storage section 21 of FIG. 2F is different from that of FIG. 2E in that a heat insulating material 211 is disposed over the entire upper surface of the metal material 203, and the heat insulating material 202 is disposed on the heat insulating material 211. The thickness of the heat insulating material 211 can be set to a thickness in which an air layer 212 (second air layer) is formed between the lower surface of the sample container 61 and the upper surface of the heat insulating material 211. A thickness e of the air layer 212 is defined as a distance from the interfaces between the inner bottom sections of the sample container 61 and the samples 63 to the upper surface of the heat insulating material 211. In the cultivation container storage section 21 of FIG. 2F, the thickness a of the air layer 206 may be smaller than the thickness e of the air layer 212.

Also in the structure of FIG. 2F, the supply amount of the thermal energy to the lower surface of the sample container 61 can be decreased, and thus the occurrence of the dew condensation can be prevented.

As described above, in FIGS. 2A to 2E, the heat insulating material 202 is installed on the metal material 203, but a configuration in which a supporting member that suspends the heat insulating material 202 is further provided to the lower surface of the metal material 201, and the cultivation container 6 is placed on the suspended heat insulating material 202 may be possible. The heat insulating material 202 may be fixed to the metal material 204 and the metal material 205.

In the cultivation container storage section 21 of the present embodiment, the configurations of FIGS. 2A to 2F may be combined so that the thermal energy supplied to the interface between the open end of the sample container 61 and the lid 62 becomes greater than the thermal energy supplied to the interfaces between the inner bottom sections of the sample container 61 and the samples 63. For example, FIGS. 2A and 2D can be combined to obtain a configuration of disposing the air layer 208 only under the sample container 61.

According to the present embodiment, as illustrated in FIG. 1A, the temperature control section 5 may be disposed on the upper part of the analyzing device 1 to form a temperature gradient in which the temperature decreases as it goes from the upper stage to the lower stage of the cultivation container rack 2. The temperature control section 5 may be disposed immediately above the cultivation container rack 2 to more effectively form the temperature gradient from the upper stage to the lower stage of the cultivation container rack 2. In a general incubator, the internal temperature is controlled so that the temperature gradient is not generated, but by increasing the temperature to the upper stage of the cultivation container rack 2 in a degree of not affecting the cultivation of the samples 63, it is possible to cause the thermal energy supplied to the interfaces between the inner bottom sections of the sample container 61 and the samples 63 to be lower than the thermal energy supplied to the interface between the open end of the sample container 61 and the lid 62. Accordingly, the dew condensation can be prevented.

As described above, the cultivation container storage section 21 of the present embodiment is configured so that the thermal energy supplied to the interfaces between the inner bottom sections of the sample container 61 and the samples 63 is higher than the thermal energy supplied to the interface between the open end of the sample container 61 and the lid 62. Accordingly, the time for removing or preventing the dew condensation on the cultivation container 6 that occurs during the cultivation time becomes unnecessary, the cultivation container 6 can be instantly supplied to the sample measuring section 42, and thus measurement can be effectively performed. According to the above configuration, it is not required to provide a mechanism for removing the dew condensation, and thus the size or the cost of the analyzing device 1 does not increase. Since the dew condensation is prevented, the accuracy of the measurement result is improved, and it is not required to open the lid 62 in order to remove the dew condensation. Therefore, contamination can be prevented.

Second Embodiment

Subsequently, an analyzing device according to a second embodiment is described with reference to FIGS. 3A to 3H. The analyzing device according to the second embodiment different from that according to the first embodiment in that the cultivation container rack 2 further includes a heat source 213 and a temperature sensor 214. FIGS. 3A to 3H illustrate an example of using the cultivation container storage sections 21 illustrated in FIG. 2D, but the other configuration example (FIG. 2A to 2C, 2E, or 2F) of the cultivation container storage section 21 may be used.

FIG. 3A is a schematic front view illustrating a disposition example of the heat source 213 and the temperature sensor 214 according to the second embodiment. As illustrated in FIG. 3A, the cultivation container rack 2 further includes the heat sources 213a to 213d and the temperature sensors 214a to 214d.

The heat sources 213a and 213c are provided to cover the entire left side surface of the cultivation container rack 2, and the heat sources 213b and 213d are provided to cover the entire right side surface of the cultivation container rack 2. In other words, the heat sources 213a and 213c are provided on the outer wall surface of the metal material 204, and the heat sources 213b and 213d are provided on the outer wall surface of the metal material 205.

As the heat sources 213a to 213d, for example, heaters such as electric heaters, ceramic heaters, silicon rubber heaters, sheathed heaters, band heaters, polyimide heaters, space heaters, cord heaters, cartridge heaters, and metal embedded heaters, and Peltier are used. The heat sources 213a to 213d are provided on the side surface of the cultivation container rack 2 by a double-sided tape, a heat conductive sheet, a bond, or the like (not illustrated) and are in contact with the metal materials 201, 204, and 205.

Though not illustrated, a metal layer or a resin layer is disposed on the surfaces of the heat sources 213a to 213d.

The temperature sensors 214a to 214d measure the internal temperatures of the cultivation container storage sections 21. The figure on the right side of FIG. 3A is an enlarged view of the cultivation container storage section 21 provided with the temperature sensors 214a and 214b. As illustrated in FIG. 3A, in the cultivation container storage section 21 on the second stage from the top of the cultivation container rack 2, the temperature sensor 214a is disposed on the inner wall surface of the metal material 204, and the temperature sensor 214b is disposed on the inner wall surface of the metal material 205. In the cultivation container storage section 21 on the sixth from the top, the temperature sensor 214c is disposed on the inner wall surface of the metal material 204, and the temperature sensor 214d is disposed on the inner wall surface of the metal material 205. The positions of the heat sources 213a to 213d and the temperature sensors 214a to 214d are not limited to the positions of FIG. 3A.

FIG. 3B is a block diagram illustrating control mechanisms of the heat sources 213a to 213d and the temperature sensors 214a to 214d of FIG. 3A. As illustrated in FIG. 3B, the heat sources 213a to 213d and the temperature sensors 214a to 214d are connected to the control section 7, respectively. The temperature sensors 214a to 214d output measured values of the temperatures to the control section 7. The control section 7 receives the measured values of the temperatures from the temperature sensors 214a to 214d and controls the amount of current, the amount of voltage, and the like corresponding to the heat quantities supplied to the heat sources 213a to 213d, based on the measured values.

The control section 7 may control the heat quantities supplied to the heat sources 213a to 213d to form the temperature gradient in which the temperature decreases as it goes from the upper stage to the lower stage of the cultivation container rack 2. Accordingly, in the cultivation container storage section 21 on each stage, it is possible to cause the thermal energy supplied to the interfaces between the inner bottom sections of the sample container 61 and the samples 63 to be lower than the thermal energy supplied to the interface between the open end of the sample container 61 and the lid 62, more effectively. The heat sources 213a to 213d may be configured so that the supplied heat quantity decreases from the upper part to the lower part. Here, as the heat sources 213a to 213d, for example, an electric heater configured so that the number of turns decreases from the upper part to the lower part can be used.

In FIG. 3A, four heat sources of the heat sources 213a to 213d and four temperature sensors of the temperature sensors 214a to 214d are disposed, but each number of the heat source 213 and the temperature sensor 214 may be one or more. The number of the heat sources 213 may be smaller than the number of the temperature sensors 214.

If the number of the temperature sensors 214 is larger than the number of the heat sources 213, the control section 7 controls the amount of current or the amount of voltage corresponding to the heat quantities to be supplied to the heat source 213, based on output values such as the lowest output value and the highest output value in the plurality of temperature sensors 214 and the average value or the sum of the output values of the plurality of temperature sensors 214.

As described above, the cultivation container storage sections 21 illustrated in FIG. 3A can increase the supply amount of the thermal energy compared with the first embodiment, and thus it is possible to accelerate the temperature rise of the metal material 201. Accordingly, the occurrence of the dew condensation can be more effectively prevented.

FIG. 3C is a schematic front view illustrating another disposition example of the heat source 213 and the temperature sensor 214 according to the second embodiment. The example of FIG. 3C is different from that of FIG. 3A in that one temperature sensor 214 is disposed only in the central part the cultivation container rack 2 (the cultivation container storage section 21 on the fifth stage).

The figure on the right side of FIG. 3C is an enlarged view of the cultivation container storage section 21 in which the temperature sensor 214 is provided. As illustrated in the figure on the right side of FIG. 3C, for example, the temperature sensor 214 is installed on the lower surface of the metal material 201.

FIG. 3D is a block diagram illustrating control mechanisms of the heat sources 213a to 213d and the temperature sensor 214 of FIG. 3C. In the same manner as the above, the amount of current and the amount of voltage supplied to the heat sources 213a to 213d are controlled based on the output of the temperature sensor 214. The others are the same as described above, and thus the descriptions thereof are omitted.

FIG. 3E is a schematic front view illustrating still another disposition example of the heat source 213 and the temperature sensor 214 according to the second embodiment. The cultivation container rack 2 described above includes one column of the cultivation container storage sections 21 of eight stages arranged in the height direction, but the cultivation container rack 2 of FIG. 3E includes two columns of the cultivation container storage sections 21 of eight stages, and the cultivation container storage sections 21 are disposed also in the horizontal direction. As illustrated in FIG. 3E, the metal materials 205 of the cultivation container storage sections 21 of the column on the left side and the metal materials 204 of the cultivation container storage sections 21 of the column on the right side are disposed to be in contact with each other. The number of columns of the cultivation container storage sections 21 is not limited to two, and may be any number.

The heat sources 213a and 213c are provided on the metal materials 204 of the cultivation container storage sections 21 of the column on the left side, and the heat sources 213b and 213d are provided on the metal materials 205 of the cultivation container storage sections 21 of the column on the right side. A heat source 213e is disposed on the upper surface of the cultivation container storage section 21 of the uppermost stage, and a heat source 213f is disposed on the lower surface of the cultivation container storage section 21 of the lowermost stage.

The temperature sensors 214a to 214f are disposed near the heat sources 213a to 213f inside the cultivation container storage sections 21, respectively.

As such, if the cultivation container storage sections 21 are disposed in the height direction and the horizontal direction, the supply amount to the central part of the cultivation container rack 2 can be secured by providing the heat sources 213e and 213f respectively on the top and the bottom of the cultivation container rack 2 as illustrated in FIG. 3E.

FIG. 3F is a block diagram illustrating control mechanisms of the heat sources 213a to 213f and the temperature sensors 214a to 214f of FIG. 3E. As illustrated in FIG. 3F, the heat sources 213a to 213f are controlled by the control section 7 of the analyzing device 1 based on the outputs of the temperature sensors 214a to 214f. The other points are the same as described above, and the descriptions thereof are omitted.

FIG. 3G is a schematic front view illustrating another disposition example of the heat source 213 and the temperature sensor 214 according to the second embodiment. The example of FIG. 3G is different from FIG. 3E, in that one the temperature sensor 214 is disposed on the central part of the cultivation container rack 2.

FIG. 3H is a block diagram illustrating control mechanisms of the heat sources 213a to 213f and the temperature sensor 214 of FIG. 3G. As illustrated in FIG. 3H, the heat sources 213a to 213f are controlled by the control section 7 of the analyzing device 1 based on the output of the temperature sensor 214. The other points are as described above, and thus the descriptions thereof are omitted.

As described above, according to the present embodiment, the heat sources 213 are provided directly in the cultivation container storage sections 21, but metal plates and the like are disposed between the heat sources 213 and the cultivation container storage sections 21, so that the thermal energy of the heat source 213 is supplied to the cultivation container storage sections 21 via the metal plates.

As described above, according to the present embodiment, since the cultivation container rack 2 includes the heat source 213 and the temperature sensor 214, the supply amount of the thermal energy can be increased compared with the first embodiment, and thus it is possible to accelerate the temperature rise of the metal material 201. Accordingly, the occurrence of the dew condensation in the dew condensation occurrence section can be effectively prevented. By controlling the supplied heat quantity by the heat source 213 to form the temperature gradient so that the temperature decreases from the upper stage to the lower stage of the cultivation container rack 2, the occurrence of the dew condensation can be more effectively prevented.

Modification

The present disclosure is not limited to the embodiments described above, but includes various modifications. For example, the embodiments described above are specifically described for better understanding of the present disclosure and are not required to necessarily include all the configurations described above. A part of a certain embodiment can be replaced with a configuration of another embodiment. It is also possible to add a configuration of another embodiment to a configuration of a certain embodiment. It is also possible to add, delete, or replace a part of the configuration of another embodiment with respect to a part of the configuration of each embodiment.

REFERENCE SIGNS LIST

1: analyzing device
2: cultivation container rack
3: conveyance section
4: measuring section
5: temperature control section
6: cultivation container
7: control section
21: cultivation container storage section
22: leg section
31, 32: actuator
33: holding section
41: measuring unit
42: sample measuring section

51: heater
52: heat sink
53: fan
54: wind
61: sample container
62: lid
63: sample
201, 203, 204, 205: metal material
202, 209, 211: heat insulating material
206 to 208, 210, 212: air layer
213: heat source
214: temperature sensor
The invention claimed is:

1. A cultivation container rack comprising:
a cultivation container;
at least one cultivation container storage section, in an interior area of which the cultivation container is disposed, wherein each of the at least one cultivation container storage section includes
a first member that configures a top of the at least one cultivation container storage section disposed above the cultivation container,
a second member that configures a bottom of the at least one cultivation container storage section and is parallel to the first member,
a third member that is disposed between the first member and the second member, the third member being disposed below the cultivation container such that an upper surface of the third member is in contact with a lower surface of the cultivation container,
a fourth member connected to the first, second and third members at a first lateral end of the first, second and third members,
a fifth member connected to the first, second and third members at a second lateral end of the first, second and third members, the second lateral end being opposite from the first lateral end, wherein the interior area is delimited by the first, second, fourth and fifth members,
a first heat source that is installed on an exterior surface of the fourth member and a second heat source that is installed on an exterior surface of the fifth member of the at least one cultivation container storage section, and
a first temperature sensor that is disposed on an interior surface of the first member and the fourth member of the at least one cultivation container storage section and a second temperature sensor that is disposed on the interior surface of the first member and an interior surface of the fifth member of the at least one cultivation container storage section,
wherein the third member is arranged so that a distance in a height direction of the at least one cultivation container storage direction between the first member and the cultivation container is no greater than a distance in the height direction between the second member and the cultivation container.

2. The cultivation container rack according to claim 1, wherein a thermal conductivity of the third member is lower than a thermal conductivity of the first member and a thermal conductivity of the second member.

3. The cultivation container rack according to claim 1, wherein the third member includes a recessed portion that is separated from the lower surface of the cultivation container.

4. The cultivation container rack according to claim 1, wherein a material of the first member and a material of the second member are the same, and the distance in the height direction between the first member and the cultivation container is less than the distance in the height direction between the second member and the cultivation container.

5. An analyzing device comprising:
the cultivation container rack according to claim 1;
a conveyance section that conveys the cultivation container to and from the cultivation container rack;
a measuring section to which the cultivation container is conveyed from the cultivation container rack and which measures a cultivation state of a sample in the cultivation container;
a temperature control section, including a heater, a heat sink and a fan, that controls a temperature inside the analyzing device; and
a controller coupled to, and configured to control operation of, the cultivation container rack, the conveyance section, the measuring section and the temperature control section.

6. The analyzing device according to claim 5, wherein
the at least one cultivation container storage section includes a plurality of cultivation container storage sections stacked in the height direction, and
the temperature control section controls the heat source to supply heat so that a temperature gradient occurs from an upper cultivation storage container section to a lower cultivation storage container section of the plurality of cultivation container storage sections.

7. A cultivation container rack comprising:
a cultivation container;
at least one cultivation container storage section, in an interior area of which the cultivation container is disposed, wherein each of the at least one cultivation container storage section includes
a first member that configures a top of the at least one cultivation container storage section disposed above the cultivation container,
a second member that configures a bottom of the at least one cultivation container storage section and is parallel to the first member,
a third member that is disposed between the first member and the second member, the third member being disposed below the cultivation container such that an upper surface of the third member is in contact with a lower surface of the cultivation container,
a fourth member connected to the first, second and third members at a first lateral end of the first, second and third members, and
a fifth member connected to the first, second and third members at a second lateral end of the first, second and third members, the second lateral end being opposite from the first lateral end,
a thermal conductivity of the first member is higher than a thermal conductivity of the second member, and
a thermal conductivity of the third member is lower than the thermal conductivity of the first member and the thermal conductivity of the second member.

8. An analyzing device comprising:
the cultivation container rack according to claim 7;
a conveyance section that conveys the cultivation container to and from the cultivation container rack;
a measuring section to which the cultivation container is conveyed from the cultivation container rack and which measures a cultivation state of a sample in the cultivation container;
a temperature control section, including a heater, a heat sink and a fan, that controls a temperature inside the analyzing device; and a controller coupled to, and configured to control operation of, the cultivation container rack, the conveyance section, the measuring section and the temperature control section.

9. A cultivation container rack comprising:

a cultivation container;

at least one cultivation container storage section, in an interior area of which the cultivation container is disposed, wherein each of the at least one cultivation container storage section includes a first member that configures a top of the at least one cultivation container storage section disposed above the cultivation container, a second member that configures a bottom of the at least one cultivation container storage section and is parallel to the first member, a third member that is disposed between the first member and the second member, the third member being disposed below the cultivation container such that an upper surface of the third member is in contact with a lower surface of the cultivation container, a fourth member connected to the first, second and third members at a first lateral end of the first, second and third members, and a fifth member connected to the first, second and third members at a second lateral end of the first, second and third members, the second lateral end being opposite from the first lateral end, an upper surface of the cultivation container and a lower surface of the first member are spaced apart from each other, an emissivity of thermal energy of the first member is higher than an emissivity of thermal energy of the second member, a thermal conductivity of the first member is higher than a thermal conductivity of the second member, and a central portion of the third member is spaced apart from a lower part of the cultivation container.

10. The cultivation container rack according to claim 9, wherein a distance between the central portion of the third member and the lower part of the cultivation container is greater than a distance between the upper surface of the cultivation container and the lower surface of the first member.

11. An analyzing device comprising:

the cultivation container rack according to claim 9;

a conveyance section that conveys the cultivation container to and from the cultivation container rack;

a measuring section to which the cultivation container is conveyed from the cultivation container rack and which measures a cultivation state of a sample in the cultivation container;

a temperature control section, including a heater, a heat sink and a fan, that controls a temperature inside the analyzing device; and a controller coupled to, and configured to control operation of, the cultivation container rack, the conveyance section, the measuring section and the temperature control section.

12. A cultivation container rack comprising:

a cultivation container; and at least one cultivation container storage section, in an interior area of which the cultivation container is disposed, wherein each of the at least one cultivation container storage section includes a first member that configures a top of the at least one cultivation container storage section disposed above the cultivation container, a second member that configures a bottom of the at least one cultivation container storage section and is parallel to the first member, a third member that is disposed between the first member and the second member, the third member being disposed below the cultivation container such that an upper surface of the third member is in contact with a lower surface of the cultivation container, a fourth member connected to the first, second and third members at a first lateral end of the first, second and third members, and a fifth member connected to the first, second and third members at a second lateral end of the first, second and third members, the second lateral end being opposite from the first lateral end, an emissivity of thermal energy of the first member that faces the cultivation container is higher than an emissivity of thermal energy of the second member that faces the cultivation container, and a central portion of the third member is spaced apart from a lower part of the cultivation container.

13. The cultivation container rack according to claim 12, wherein an upper surface of the cultivation container is spaced apart from a lower surface of the first member.

14. An analyzing device comprising:

the cultivation container rack according to claim 12;

a conveyance section connected to the cultivation container rack that conveys the cultivation container to and from the cultivation container rack;

a measuring section to which the cultivation container is conveyed from the cultivation container rack, and which measures a cultivation state of a sample in the cultivation container; and a temperature control section, including a heater, a heat sink and a fan, that controls a temperature inside the analyzing device; and a controller coupled to, and configured to control operation of, the cultivation container rack, the conveyance section, the measuring section and the temperature control section.

* * * * *